United States Patent
Cho et al.

(10) Patent No.: US 7,254,426 B2
(45) Date of Patent: *Aug. 7, 2007

(54) BLOOD SUGAR LEVEL MEASURING APPARATUS

(75) Inventors: Ok-Kyung Cho, Schwerte (DE); Yoon-Ok Kim, Schwerte (DE)

(73) Assignee: Hitachi, Ltd., Tokyo (JP)

( * ) Notice: Subject to any disclaimer, the term of this patent is extended or adjusted under 35 U.S.C. 154(b) by 846 days.

This patent is subject to a terminal disclaimer.

(21) Appl. No.: 10/620,689

(22) Filed: Jul. 17, 2003

(65) Prior Publication Data

US 2004/0225209 A1 Nov. 11, 2004

(30) Foreign Application Priority Data

May 7, 2003 (JP) ............................ 2003-129020

(51) Int. Cl.
*A61B 5/00* (2006.01)
(52) U.S. Cl. .................. 600/316; 600/365; 600/326
(58) Field of Classification Search ............... 600/310, 600/316, 322, 323, 326, 365, 549
See application file for complete search history.

(56) References Cited

U.S. PATENT DOCUMENTS

| | | | |
|---|---|---|---|
| 4,306,569 A | 12/1981 | Weil | |
| 4,333,803 A | 6/1982 | Seger | |
| 4,509,531 A | 4/1985 | Ward | |
| 4,750,140 A | 6/1988 | Asano | |
| 4,802,489 A | 2/1989 | Nitzan | |
| 4,859,078 A * | 8/1989 | Bowman et al. ............ | 600/549 |
| 5,410,291 A * | 4/1995 | Kuzuoka .................... | 374/185 |
| 5,551,422 A | 9/1996 | Simonsen | |
| 5,576,544 A | 11/1996 | Rosenthal | |
| 5,676,143 A | 10/1997 | Simonsen | |
| 5,725,480 A | 3/1998 | Oosta | |
| 5,732,711 A | 3/1998 | Fitzpatrick | |
| 5,743,262 A | 4/1998 | Lepper, Jr. | |
| 5,769,784 A | 6/1998 | Barnett | |
| 5,795,305 A | 8/1998 | Cho et al. ................... | 600/549 |
| 5,857,966 A | 1/1999 | Clawson | |
| 5,899,855 A | 5/1999 | Brown | |
| 5,924,996 A | 7/1999 | Cho et al. ................... | 600/549 |
| 6,129,673 A * | 10/2000 | Fraden ....................... | 600/549 |

(Continued)

FOREIGN PATENT DOCUMENTS

EP 0 387 630 9/1990

(Continued)

OTHER PUBLICATIONS

Hillson, R.M., "Facial and Sublingual Temperature Changes Following Intravenous Glucose Injection in Diabetics", Diabete & Metabolisme (Paris) 1982, vol. 8, pp. 15-19.

(Continued)

*Primary Examiner*—Eric F Winakur
(74) *Attorney, Agent, or Firm*—Antonelli, Terry, Stout & Kraus, LLP.

(57) ABSTRACT

Blood sugar levels are non-invasively measured based on temperature measurements. Blood sugar levels obtained by non-invasive measurements of temperatures are corrected by blood oxygen saturation and the volume of blood flow so that the measurement data can be stabilized.

21 Claims, 8 Drawing Sheets

U.S. PATENT DOCUMENTS

| | | |
|---|---|---|
| 6,226,089 B1 | 5/2001 | Hakamata |
| 6,240,306 B1 | 5/2001 | Rohrscheib |
| 6,269,314 B1 | 7/2001 | Iitawaki et al. |
| 6,270,455 B1 | 8/2001 | Brown |
| 6,280,381 B1 | 8/2001 | Malin |
| 6,353,226 B1 | 3/2002 | Khalil |
| 6,512,936 B1 | 1/2003 | Monfre et al. |
| 6,551,276 B1 | 4/2003 | Mann et al. |
| 6,615,061 B1 | 9/2003 | Khalil |
| 2002/0016534 A1 | 2/2002 | Trepagnier et al. |
| 2002/0183646 A1 | 12/2002 | Stivoric et al. |
| 2003/0010898 A1 | 1/2003 | MacKenzie et al. |
| 2003/0125612 A1 | 7/2003 | Fox et al. |
| 2003/0152133 A1 | 8/2003 | Ellenz |
| 2003/0214655 A1 | 11/2003 | Weiss et al. |
| 2004/0009100 A1 | 1/2004 | Simons et al. |

FOREIGN PATENT DOCUMENTS

| | | |
|---|---|---|
| EP | 0 778 000 A1 | 6/1997 |
| GB | 1502056 | 2/1978 |
| JP | 06 317566 | 11/1994 |
| JP | 7-71945 | 3/1995 |
| JP | 08 322821 | 12/1996 |
| JP | 10-33512 | 2/1998 |
| JP | 10-108857 | 4/1998 |
| JP | 11 505451 | 5/1999 |
| JP | 11 155840 | 6/1999 |
| JP | 11-230901 | 8/1999 |
| JP | 11 318872 | 11/1999 |
| JP | 2000 074829 | 3/2000 |
| JP | 2000 506048 | 5/2000 |
| JP | 2000-258343 | 9/2000 |
| JP | 2002 535023 | 10/2002 |
| JP | 2003 510556 | 3/2003 |
| WO | 9 641151 | 12/1996 |
| WO | 01/28417 | 4/2001 |
| WO | WO 01/28414 | 4/2001 |
| WO | WO 02/25233 | 3/2002 |
| WO | 03/010510 | 2/2003 |
| WO | WO 03/010510 | 2/2003 |

OTHER PUBLICATIONS

Scott, A.R., "Diabetes Mellitus and Thermoregulation[1]", Can. J. Physiol. Pharmacol., vol. 65, 1987, pp. 1365-1376.

Journal of the Medical Association of Thailand, vol. 69, No. 3, 1986, pp. 153-157 (Abstract).

* cited by examiner

BLOOD SUGAR LEVEL MEASURING APPARATUS

BACKGROUND OF THE INVENTION

1. Field of the Invention

The present invention relates to a method and apparatus for non-invasively measuring glucose concentration in a living body without blood sampling.

2. Background Art

Hilson et al. report facial and sublingual temperature changes in diabetics following intravenous glucose injection (non-patent literature 1). Scott et al. discuss the issue of diabetes mellitus and thermoregulation (non-patent literature 2). Based on such researches, Cho et al. suggests a method and apparatus for determining blood glucose concentration by temperature measurement without requiring the collection of a blood sample (patent literature 1 and 2).

Various other attempts have been made to determine glucose concentration without blood sampling. For example, a method has been suggested (patent literature 3) whereby a measurement site is irradiated with near-infrared light of three wavelengths, and the intensity of transmitted light as well as the temperature of the living body is detected. Then, representative values of the second-order differentiated values of absorbance are calculated, and the representative values are corrected in accordance with the difference of the living body temperature from a predetermined reference temperature. The blood sugar level corresponding to the thus corrected representative values is then determined. An apparatus is also provided (patent literature 4) whereby a measurement site is heated or cooled while monitoring the living body temperature. The degree of attenuation of light based on light irradiation is measured at the moment of temperature change so that the glucose concentration responsible for the temperature-dependency of the degree of light attenuation can be measured. Further, an apparatus is reported (patent literature 5) whereby an output ratio between reference light and the light transmitted by an irradiated sample is taken, and then the glucose concentration is calculated by a linear expression of the logarithm of the output ratio and the living body temperature.

(Non-patent literature 1)
R. M. Hilson and T. D. R. Hockaday, "Facial and sublingual temperature changes following intravenous glucose injection in diabetics," Diabete & Metabolisme, 8, pp.15-19: 1982

(Non-patent literature 2)
A. R. Scott, T. Bennett, I. A. MacDonald, "Diabetes mellitus and thermoregulation," Can. J. Physiol. Pharmacol., 65, pp. 1365-1376: 1987

(Patent Literature 1)
U.S. Pat. No. 5,924,996
(Patent Literature 2)
U.S. Pat. No. 5,795,305
(Patent Literature 3)
JP Patent Publication (Kokai) No. 2000-258343 A
(Patent Literature 4)
JP Patent Publication (Kokai) No. 10-33512 A (1998)
(Patent Literature 5)
JP Patent Publication (Kokai) No. 10-108857 A (1998)

Glucose (blood sugar) in the blood is used for glucose oxidation reaction in cells to produce necessary energy for the maintenance of living bodies. In the basal metabolism state, in particular, most of the produced energy is converted into heat energy for the maintenance of body temperature. Thus, it can be expected that there is some relationship between blood glucose concentration and body temperature. However, as is evident from the way sicknesses cause fever, the body temperature also varies due to factors other than blood glucose concentration. While methods have been proposed to determine blood glucose concentration by temperature measurement without blood sampling, they lack sufficient accuracy.

SUMMARY OF THE INVENTION

It is the object of the invention to provide a method and apparatus for determining blood glucose concentration with high accuracy based on temperature data of subjects without blood sampling.

Blood sugar is delivered to the cells in the entire human body via the blood vessel system, particularly the capillary blood vessels. In the human body, complex metabolic pathways exist. Glucose oxidation is a reaction in which, fundamentally, blood sugar reacts with oxygen to produce water, carbon dioxide, and energy. Oxygen herein refers to the oxygen delivered to the cells via blood. The volume of oxygen supply is determined by the blood hemoglobin concentration, the hemoglobin oxygen saturation, and the volume of blood flow. On the other hand, the heat produced in the body by glucose oxidation is dissipated from the body by convection, heat radiation, conduction, and so on. On the assumption that the body temperature is determined by the balance between the amount of energy produced in the body by glucose burning, namely heat production, and heat dissipation such as mentioned above, we set up the following model:

(1) The amount of heat production and the amount of heat dissipation are considered equal.
(2) The amount of heat production is a function of the blood glucose concentration and the volume of oxygen supply.
(3) The volume of oxygen supply is determined by the blood hemoglobin concentration, the blood hemoglobin oxygen saturation, and the volume of blood flow in the capillary blood vessels.
(4) The amount of heat dissipation is mainly determined by heat convection and heat radiation.

According to this model, we achieved the present invention after realizing that blood sugar levels can be accurately determined on the basis of the results of measuring the temperature of the body surface and measuring parameters relating to the blood oxygen concentration and measuring parameter relating to the blood flow volume. The parameters can be measured from a part of the human body, such as the fingertip. The parameters relating to convection and radiation can be determined by carrying out thermal measurements on the fingertip. The parameters relating to the blood hemoglobin concentration and the blood hemoglobin oxygen saturation can be determined by sepctroscopically measuring the blood hemoglobin and then finding the ratio between the hemoglobin bound with oxygen and the hemoglobin not bound with oxygen. The parameter relating to the volume of blood flow can be determined by measuring the amount of heat transfer from the skin.

In one aspect, the invention provides a blood sugar level measuring apparatus comprising:

a heat amount measuring unit for measuring a plurality of temperatures derived from a body surface in order to obtain information used for calculating the amount of convective heat transfer and the amount of radiation heat transfer concerning the dissipation of heat from the body surface;

an oxygen volume measuring unit for obtaining information concerning the volume of blood oxygen;

a storage unit for storing the relationships between blood sugar levels and individual parameters corresponding to both the multiple temperatures and blood oxygen volume;

a computing unit for converting the measurement values provided by the heat amount measuring unit and the oxygen volume measuring unit into parameters, and computing a blood sugar level by applying the parameters to the relationships stored in the storage unit; and a display unit for displaying the blood sugar level computed by the computing unit.

Preferably, the heat amount measuring unit may comprise an ambient temperature detector for measuring the ambient temperature, and a radiation temperature detector for measuring the radiation heat from the body surface.

Preferably, the oxygen volume measuring unit may comprise a blood flow volume measuring unit for obtaining information concerning the volume of blood flow, and an optical measuring unit for obtaining blood hemoglobin concentration and hemoglobin oxygen saturation.

In another aspect, the invention provides a blood sugar level measuring apparatus comprising:

a temperature measuring unit for measuring a plurality of temperatures from a body surface;

a blood flow volume measuring unit for obtaining information concerning the volume of blood flow based on the results of measurement by the temperature measuring unit;

an oxygen volume measuring unit for determining the volume of blood oxygen based on the result of measurement by the blood flow volume measuring unit;

a storage unit for storing the relationships between blood sugar levels and individual parameters corresponding to the multiple temperatures, the volume of blood oxygen and the volume of blood flow;

a computing unit for converting the measurement values provided by the temperature measuring unit, the blood flow volume measuring unit and the oxygen volume measuring unit into parameters, and computing a blood sugar level by applying the parameters to the relationships stored in the storage unit; and a display unit for displaying the blood sugar level computed by the computing unit.

In yet another aspect, the invention provides a blood sugar level measuring apparatus comprising:

an ambient temperature measuring unit for measuring the ambient temperature;

a body-surface contact unit to be brought into contact with a body surface;

a radiation heat detector for measuring the radiation heat from the body surface;

a heat conducting member disposed in contact with the body-surface contact unit;

an indirect temperature detector disposed adjacent the heat conducting member and away from the body-surface contact unit for detecting the temperature at a position distanced away from the body-surface contact unit;

a light source for irradiating the body-surface contact unit with light of at least two different wavelengths;

a photodetector for detecting reflected light produced as the light from the light source is reflected by the body surface;

a computing unit comprising a converting portion and a processing portion, wherein the converting portion converts the outputs of the indirect temperature detector, the ambient temperature measuring unit, the radiation heat detector, and the photodetector into individual parameters, and wherein the processing portion stores the relationships between the parameters and blood sugar levels in advance and computes a blood sugar level by applying the parameters to the stored relationships; and a display unit for displaying the blood sugar level produced by the computing unit.

In yet another aspect, the invention provides a blood sugar level measuring apparatus comprising:

an ambient temperature measuring unit for measuring the ambient temperature;

a body-surface contact unit to be brought into contact with a body surface;

a heat conducting member disposed in contact with a first region of the body-surface contact unit;

an indirect temperature detector disposed adjacent the heat conductive member and away from the body-surface contact unit for detecting the temperature at a position distanced away from the body-surface contact unit;

a cylindrical member disposed in contact with a second region of the body-surface contact unit and having an opening on one end thereof;

a radiation heat detector disposed adjacent the other end of the cylindrical member for measuring the radiation heat from the body surface;

a light source for irradiating the one end of the cylindrical member with light of at least two different wavelengths;

a photodetector for detecting reflected light produced by the reflection of the light by the body surface;

a computing unit comprising a converting portion and a processing portion, wherein the converting portion converts the outputs of the indirect temperature detector, the ambient temperature measuring unit, the radiation temperature detector, and the photodetector into individual parameters, and wherein the processing portion stores the relationships between the parameters and blood sugar levels in advance and computes a blood sugar level by applying the parameters to the relationships; and a display unit for displaying the blood sugar level produced by the computing unit.

In accordance with the invention, blood sugar levels can be determined non-invasively with an accuracy similar to that according to the invasive methods according to the prior art.

DESCRIPTION OF THE PREFERRED EMBODIMENTS

The invention will now be described by way of preferred embodiments thereof with reference made to the drawings.

Initially, the above-mentioned model will be described in more specific terms. Regarding the amount of heat dissipation, convective heat transfer, which is one of the main causes of heat dissipation, is related to temperature difference between the ambient (room) temperature and the body-surface temperature. The amount of heat dissipation due to radiation, another main cause of dissipation, is proportional to the fourth power of the body-surface temperature according to the Stefan-Boltzmann law. Thus, it can be seen that the amount of heat dissipation from the human body is related to the room temperature and the body-surface temperature. Another major factor related to the amount of heat production, oxygen supply, is expressed as the product of hemoglobin concentration, hemoglobin oxygen saturation, and blood flow volume.

The hemoglobin concentration can be measured by the absorbance at the wavelength at which the molar absorbance coefficient of the oxi-hemoglobin is equal to that of the deoxi-hemoglobin (equal-absorbance wavelength). The hemoglobin oxygen saturation can be measured by measuring the absorbance at the equal-absorbance wavelength and the absorbance of at least one different wavelength at which the ratio between the molar absorbance coefficient of the oxi-hemoglobin and that of the deoxi-hemoglobin is known, and then solving simultaneous equations. Namely, the hemoglobin concentration and the hemoglobin oxygen saturation can be obtained by measuring absorbance of at least two wavelengths.

The rest is the blood flow volume, which can be measured by various methods. One example will be described below.

Figure 1:
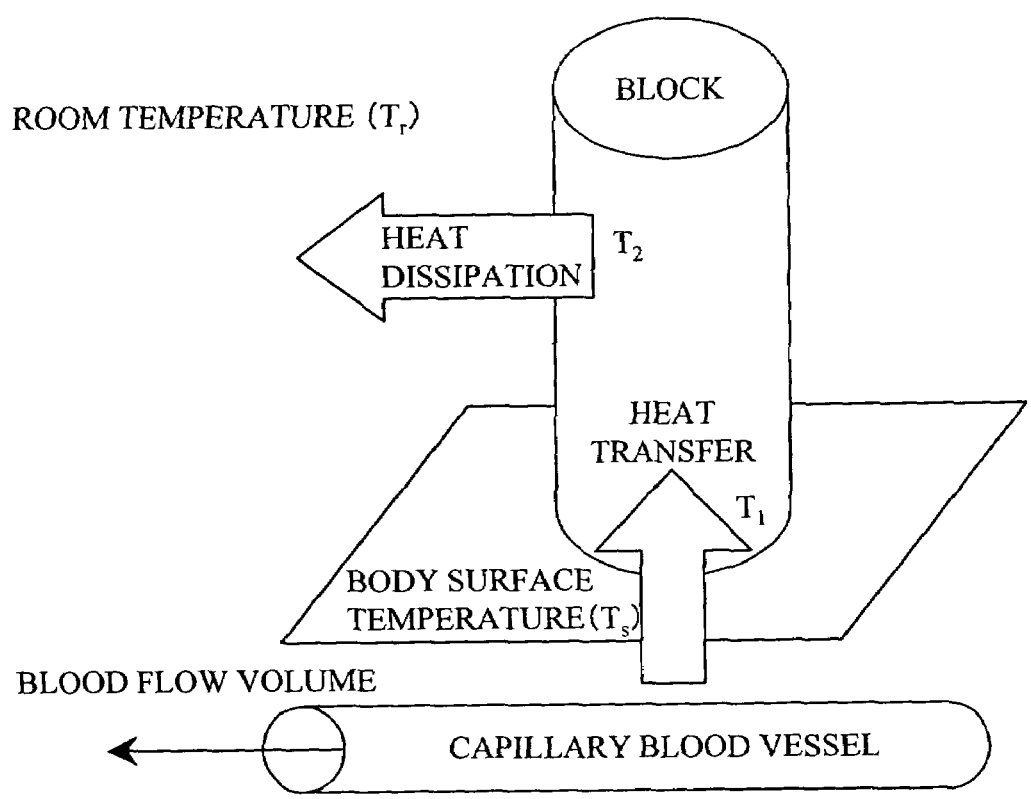
FIG. 1 shows a model of heat transfer from the body surface to a block.

FIG. 1 shows a model for the description of the transfer of heat from the body surface to a solid block having a certain heat capacity when the block is brought into contact with the body surface for a certain time and then separated. The block is made of resin such as plastic or vinyl chloride. In the illustrated example, attention will be focused on the chronological variation of the temperature $T_1$ of a portion of the block in contact with the body surface, and the chronological variation of the temperature $T_2$ of a point on the block away from the body surface. The blood flow volume can be estimated by monitoring mainly the chronological variation of the temperature $T_2$ (of a point on the spatially separated block). The details will be described later.

Before the block comes into contact with the body surface, the temperatures $T_1$ and $T_2$ at the two points of the block are equal to the room temperature $T_r$. When a body-surface temperature $T_s$ is higher than the room temperature $T_r$, the temperature $T_1$ swiftly rises due to the transfer of heat from the skin as the block contacts the body surface, and it approaches the body-surface temperature $T_s$. On the other hand, the temperature $T_2$ is less than the temperature $T_1$ as the heat conducted through the block is dissipated from the block surface, and it rises more gradually than the temperature $T_1$. The chronological variation of the temperatures $T_1$ and $T_2$ depends on the amount of heat transferred from the body surface to the block, which in turn depends on the blood flow volume in the capillary blood vessels under the skin. If the capillary blood vessels are regarded as a heat exchanger, the heat transfer coefficient from the capillary blood vessels to the surrounding cell tissues is given as a function of the blood flow volume. Thus, by measuring the amount of heat transfer from the body surface to the block by monitoring the chronological variation of the temperatures $T_1$ and $T_2$, the blood flow volume can be estimated. Accordingly, by monitoring the temperature changes in the $T_1$ and $T_2$ chronologically, and thus measuring the amount of heat transfer from the body surface to the block, the amount of heat transfer from the capillary blood vessels to the cell tissues can be estimated, so that the blood flow volume can be estimated.

Figure 2:
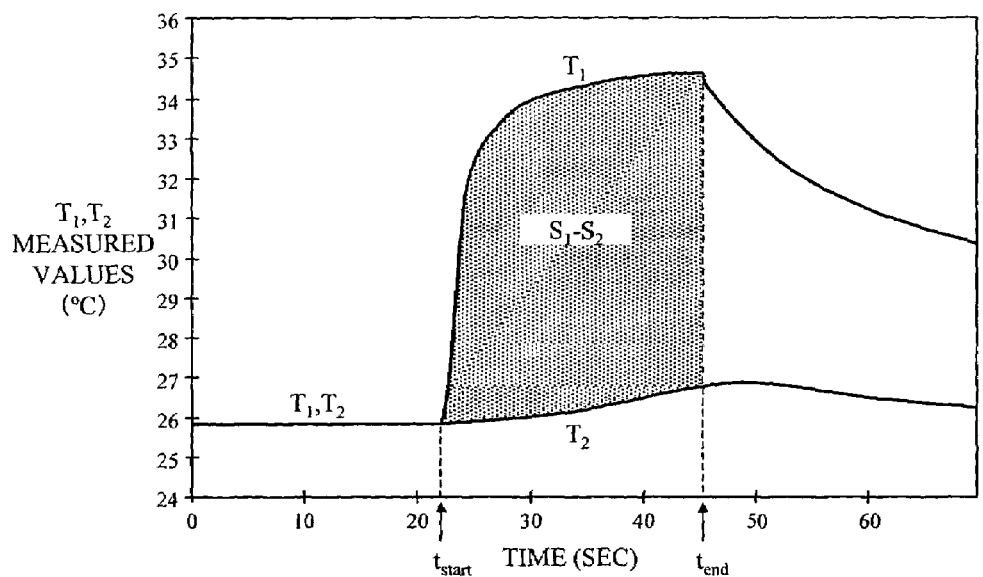
FIG. 2 plots the measurement values of temperatures $T_1$ and $T_2$ as they change with time.

FIG. 2 shows the chronological variation of the measured values of the temperature $T_1$ at the portion of the block in contact with the body surface and the temperature $T_2$ at the position on the block away from the body-surface contact position. As the block comes into contact with the body surface, the $T_1$ measured value swiftly rises, and it gradually drops as the block is brought out of contact.

Figure 3:
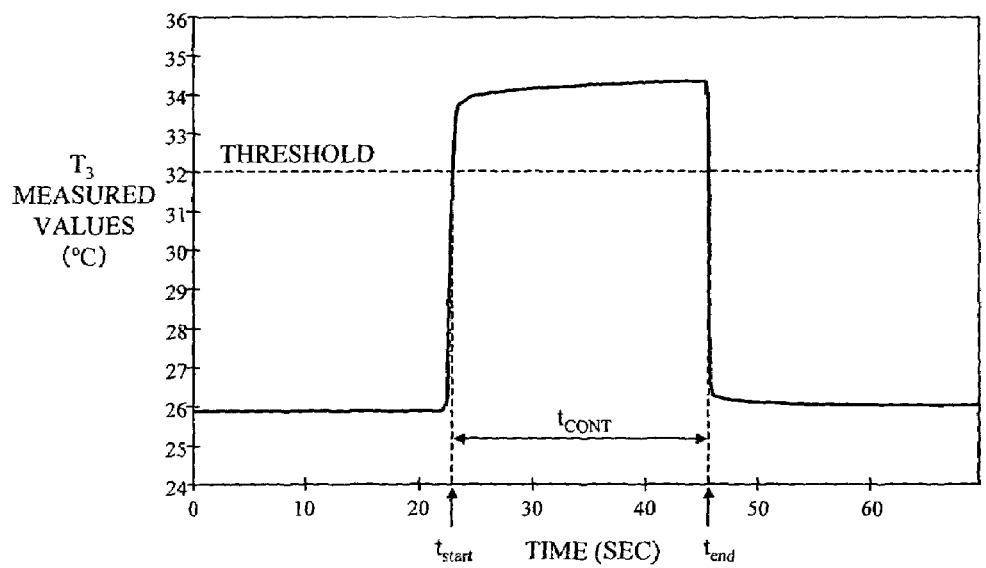
FIG. 3 shows an example of measuring the chronological change in temperature $T_3$.
Figure 7A:
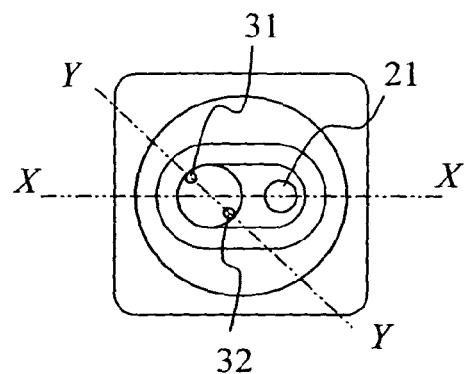
FIGS. 7(a) to 7(c) show the measuring unit in detail.
Figure 7B:
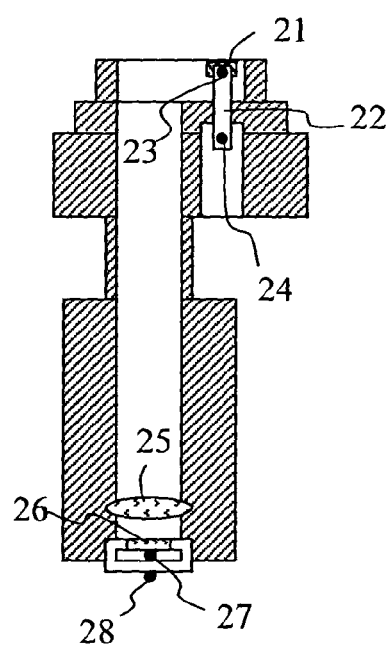
Figure 7C:
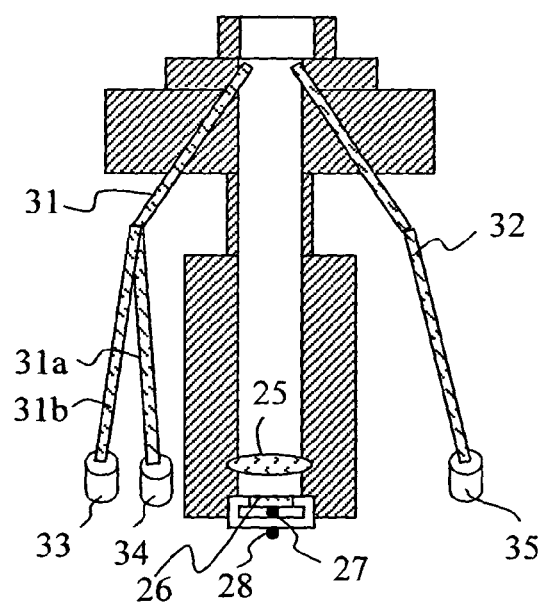

FIG. 3 shows the chronological variation of the measured value of the temperature $T_3$ measured by a radiation temperature detector. As the detector detects the temperature due to the radiation from the body surface, it is more sensitive to temperature changes than other sensors. Because radiation heat propagates as an electromagnetic wave, it can transmit temperature changes instantaneously. Thus, by locating the radiation temperature detector near where the block contacts the body surface, as shown in FIG. 7(a) to 7(c) which will be described later, the time of start of contact $t_{start}$ between the block and the body surface, and the time of end of contact $t_{end}$ can be detected by changes in the temperature $T_3$. For example, a temperature threshold value is set as shown in FIG. 3. The contact start time $t_{start}$ is when the temperature threshold value is exceeded. The contact end time $t_{end}$ is when the temperature $T_3$ drops below the threshold. The temperature threshold is set at 32° C., for example.

Then, the $T_1$ measured value between $t_{start}$ and $t_{end}$ is approximated by an S curve, such as a logistic curve. A logistic curve is expressed by the following equation:

$$T = \frac{b}{1 + c \times \exp(-a \times t)} + d$$

where T is temperature, and t is time.

The measured value can be approximated by determining factors a, b, c, and d by the non-linear least-squares method. For the resultant approximate expression, T is integrated between time $t_{start}$ and time $t_{end}$ to obtain a value $S_1$.

Similarly, an integrated value $S_2$ is calculated from the $T_2$ measured value. The smaller $(S_1-S_2)$, the larger the amount of transfer of heat from the finger surface to the position of $T_2$. $(S_1-S_2)$ becomes larger with increasing finger contact time $t_{cont}$ ($=t_{end}-t_{start}$). Thus, $a_5/(t_{cont} \times (S_1-S_2))$ is designated as a parameter $X_5$ indicating the volume of blood flow, where $a_5$ is a proportionality coefficient.

Thus, it will be seen that the measured data necessary for the determination of blood glucose concentration by the above-described model are the room temperature (ambient temperature), body surface temperature changes, temperature changes in the block brought into contact with the body surface, the temperature due to radiation from the body surface, and the absorbance of at least two wavelengths.

Figure 4:
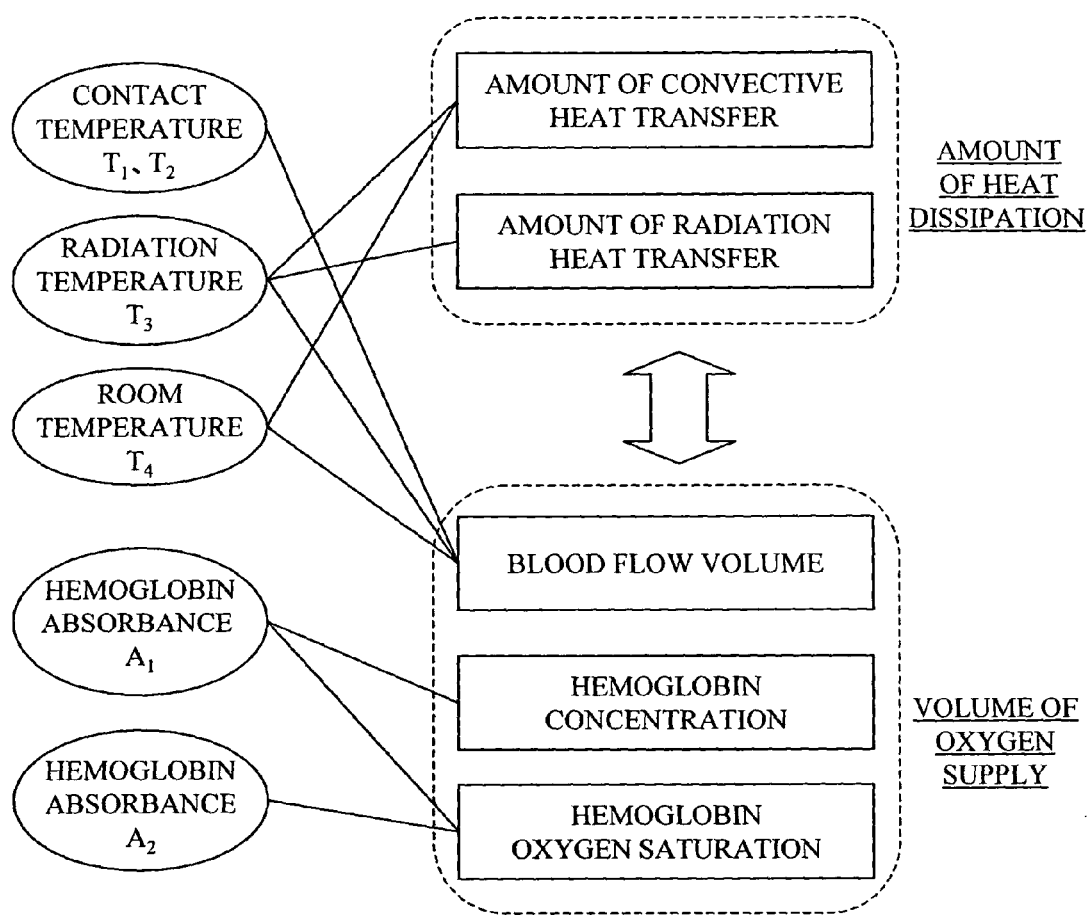
FIG. 4 shows the relationships between measurement values provided by various sensors and the parameters derived therefrom.

FIG. 4 shows the relationships between the measured values provided by various sensors and the parameters derived therefrom. A block is brought into contact with the body surface, and chronological change in two kinds of temperatures $T_1$ and $T_2$ are measured by two temperature sensors provided at two locations of the block. A radiation temperature $T_3$ on the body surface and the room temperature $T_4$ are separately measured. Absorbance $A_1$ and $A_2$ are measured at at least two wavelengths related to the absorbance of hemoglobin. The temperatures $T_1$, $T_2$, $T_3$, and $T_4$ provide parameters related to the volume of blood flow. The temperature $T_3$ provides a parameter related to the amount of heat transferred by radiation. The temperatures $T_3$ and $T_4$ provide parameters related to the amount of heat transferred by convection. The absorbance $A_1$ provides a parameter related to the hemoglobin concentration. The absorbance $A_1$ and $A_2$ provide parameters related to the hemoglobin oxygen saturation.

Hereafter, an example of apparatus for non-invasively measuring blood sugar levels according to the principle of the invention will be described.

Figure 5:
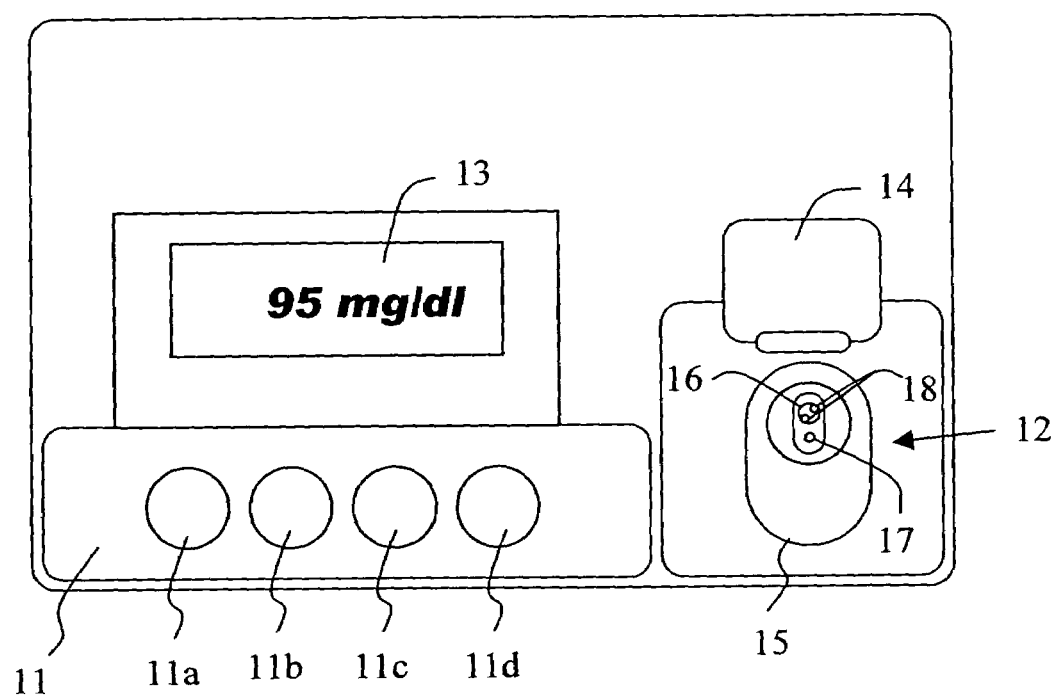
FIG. 5 shows an upper plan view of a non-invasive blood sugar level measuring apparatus according to the present invention.

FIG. 5 shows a top plan view of the non-invasive blood sugar level measuring apparatus according to the invention. While in this example the skin on the ball of the finger tip is used as the body surface, other parts of the body surface may be used.

On the top surface of the apparatus are provided an operation unit 11, a measuring unit 12 where the finger to be measured is to be placed, and a display unit 13 for displaying the state of the apparatus, measured values, and so on. The operation unit 11 includes four push buttons 11a to 11d for operating the apparatus. The measuring unit 12 has a cover 14 which, when opened (as shown), reveals a finger rest 15 with an oval periphery. The finger rest 15 accommodates an opening end 16 of a radiation temperature sensor, a contact temperature sensor 17, and an optical sensor unit 18.

Figure 6:
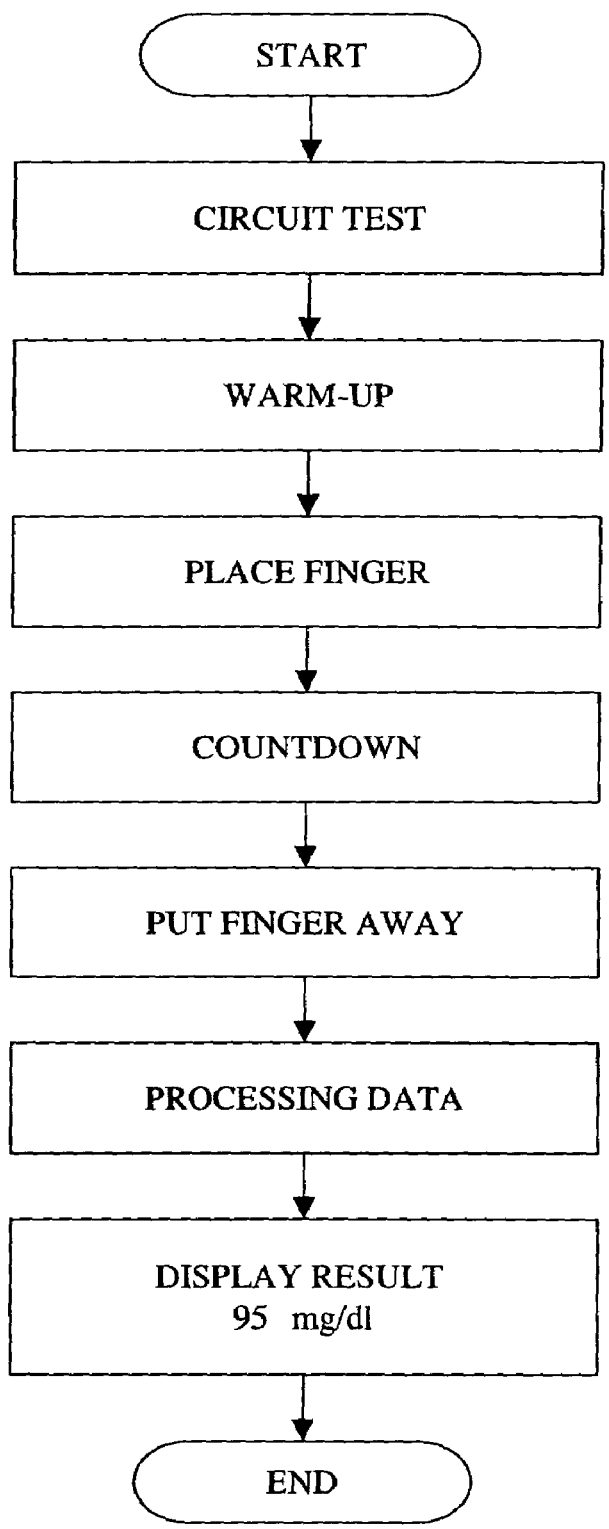
FIG. 6 shows the operating procedure for the apparatus.

FIG. 6 shows the procedure for operating the apparatus. As one of the buttons on the operation unit is depressed and the apparatus is turned on, an indication "Warming up" is displayed on the LCD while the electronic circuits in the apparatus are being warmed up. At the same time, a check program is activated to automatically check the electric circuits. As the warm-up phase is over, an indication "Place your finger" appears on the LCD. As the user places his or her finger on the finger rest, counting down begins on the LCD. When the countdown is over, an indication "Put your finger away" appears on the LCD. As the user follows the instruction, the LCD indicates "Processing data." Thereafter, the display shows the blood sugar level, which is then stored in an IC card together with the date and time. As the user took notes of the displayed blood sugar level, he or she pushes another button on the operation unit. About one minute later, the apparatus displays a message "Place your finger" on the LCD, thus indicating that the apparatus is ready for the next cycle of measurement.

FIGS. 7(a) to 7(c) show the measuring unit in detail. FIG. 7(a) is a top plan view, FIG. 7(b) is a cross section along line X-X of FIG. 7(a), and FIG. 7(c) is a cross section along line Y-Y of FIG. 7(a).

First, the process of measuring temperature by the non-invasive blood sugar level measuring apparatus according to the invention will be described. In the portion of the measuring unit where the object of measurement (ball of the finger) is to come into contact, a thin plate 21 of a highly heat-conductive material, such as gold, is placed. A bar-shaped heat-conductive member 22 made of material such as polyvinylchloride whose heat conductivity is lower than that of the plate 21 is thermally connected to the plate 21 and extends into the apparatus. The temperature sensors include a thermistor 23 for measuring the temperature of the plate 21 and acting as an adjacent temperature detector with respect to the measured object. There is also a thermistor 24 for measuring the temperature of the heat-conducting member away from the plate 21 by a certain distance and acting as an indirect temperature detector with respect to the measured object. An infrared lens 25 is disposed inside the apparatus at such a position that the measured object (ball of the finger) placed on the finger rest 15 can be seen through the lens. Below the infrared lens 25 is disposed a pyroelectric detector 27 via an infrared radiation-transmitting window 26. Another thermistor 28 is disposed near the pyroelectric detector 27.

Thus, the temperature sensor portion of the measuring unit has four temperature sensors, and they measure four kinds of temperatures as follows:

(1) Temperature on the finger surface (thermistor 23): $T_1$
(2) Temperature of the heat-conducting member (thermistor 24): $T_2$
(3) Temperature of radiation from the finger (pyroelectric detector 27): $T_3$
(4) Room temperature (thermistor 28): $T_4$ The optical sensor unit 18 measures the hemoglobin concentration and the hemoglobin oxygen saturation necessary for the determination of the oxygen supply volume. In order to measure the hemoglobin concentration and the hemoglobin oxygen saturation, absorbance must be measured at at least two wavelengths. FIG. 7(c) shows a configuration for carrying out the two-wavelength measurement using two light sources 33 and 34 and one detector 35.

The optical sensor unit 18 includes the ends of two optical fibers 31 and 32. The optical fiber 31 is for optical irradiation, and the optical fiber 32 is for receiving light. As shown in FIG. 7(c), the optical fiber 31 connects to branch fibers 31a and 31b that are provided with light-emitting diodes 33 and 34 at the respective ends thereof. The other end of the light-receiving optical fiber 32 is provided with a photodiode 35. The light-emitting diode 33 emits light with a wavelength of 810 nm, while the light-emitting diode 34 emits light with a wavelength of 950 nm. The wavelength 810 nm is the equal-absorbance wavelength at which the molar absorbance coefficient of the oxy-hemoglobin is equal to that of the deoxy-hemoglobin. The wavelength 950 nm is the wavelength at which the difference between the molar absorbance coefficient of the oxy-hemoglobin and that of the deoxy-hemoglobin is large.

The two light-emitting diodes 33 and 34 emit light in a time-sharing manner such that the finger of the subject is irradiated with the light emitted by the light-emitting diodes 33 and 34 via the irradiating optical fiber 31. The light shone on the finger is reflected by the skin, enters the light-receiving optical fiber 32, and is eventually detected by the photodiode 35. Part of the light reflected by the skin of the finger penetrates the skin and enters into the tissues and is then absorbed by the hemoglobin in the blood flowing in the capillary blood vessels. The measurement data provided by the photodiode 35 has reflectance R, and the absorbance can be approximately calculated by log(1/R). The finger is thus irradiated with light with the wavelengths of 810 nm and 950 nm, and R is measured for each and also log(1/R) is calculated for each. Thus, absorbance $A_1$ and $A_2$ for wavelengths 810 nm and 950 nm, respectively, are measured.

When the deoxy-hemoglobin concentration is [Hb] and the oxy-hemoglobin concentration is [HbO$_2$], absorbance $A_1$ and $A_2$ are expressed by the following equations:

$$A_1 = a \times ([Hb] \times A_{Hb}(810 \text{ nm}) + [HbO_2] \times A_{HbO_2}(810 \text{ nm}))$$

$$= a \times ([Hb] + [HbO_2]) \times A_{HbO_2}(810 \text{ nm})$$

-continued $$A_2 = a \times ([Hb] \times A_{Hb}(950 \text{ nm}) + [HbO_2] \times A_{HbO_2}(950 \text{ nm}))$$

$$= a \times ([Hb] + [HbO_2]) \times \left(\left(1 - \frac{[HbO_2]}{[Hb]+[HbO_2]}\right) \times\right.$$

$$\left. A_{Hb}(950 \text{ nm}) + \frac{[HbO_2]}{[Hb]+[HbO_2]} \times A_{HbO_2}(950 \text{ nm})\right)$$

$A_{Hb}(810 \text{ nm})$ and $A_{Hb}(950 \text{ nm})$, and $A_{HbO2}(810 \text{ nm})$ and $A_{HbO2}(950 \text{ nm})$ are the molar absorbance coefficients of the deoxy-hemoglobin and the oxy-hemoglobin, respectively, and are known at the respective wavelengths. The term a is a proportionality coefficient. The hemoglobin concentration [Hb]+[HbO$_2$], and the hemoglobin oxygen saturation [HbO$_2$]/([Hb]+[HbO$_2$]) can be determined from the above equations as follows:

$$[Hb] + [HbO_2] = \frac{A_1}{a \times A_{HbO_2}(810 \text{ nm})}$$

$$\frac{[HbO_2]}{[Hb]+[HbO_2]} = \frac{A_2 \times A_{HbO_2}(810 \text{ nm}) - A_1 \times A_{Hb}(950 \text{ nm}))}{A_1 \times (A_{HbO_2}(950 \text{ nm}) - A_{Hb}(950 \text{ nm}))}$$

In the present example, the hemoglobin concentration and the hemoglobin oxygen saturation are measured by measuring absorbance at two wavelengths. Preferably, however, absorbance may be measured at more than two wavelengths so that the influence of interfering components can be reduced and measurement accuracy can be improved.

Figure 8:
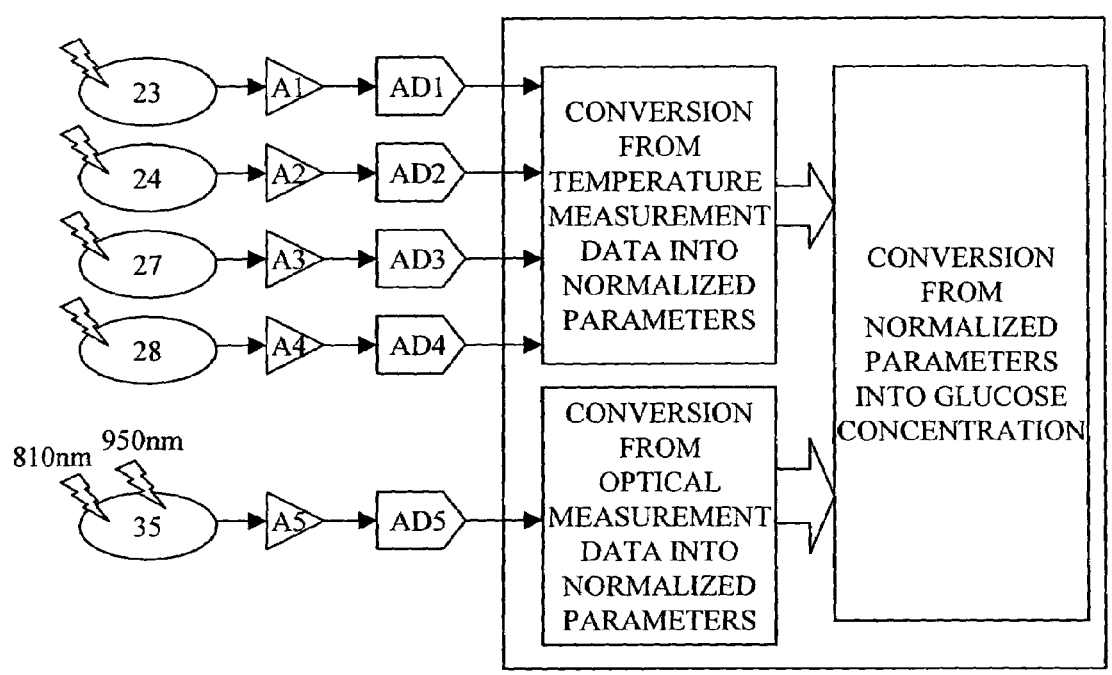
FIG. 8 shows a conceptual chart illustrating the flow of data processing in the apparatus.

FIG. 8 shows the concept of how data is processed in the apparatus. The apparatus according to the present example is equipped with five sensors, namely thermistor 23, thermistor 24, pyroelectric detector 27, thermistor 28, and photodiode 35. The photodiode 35 measures absorbance at wavelengths 810 nm and 950 nm. Thus, the apparatus is supplied with six kinds of measurement values.

The five kinds of analog signals are supplied via individual amplifiers $A_1$ to $A_5$ to analog/digital converters $AD_1$ to $AD_5$, where they are converted into digital signals. Based on the digitally converted values, parameters $x_i$ (i=1, 2, 3, 4, 5) are calculated. The following are specific descriptions of $x_i$ (where $a_1$ to $a_5$ are proportionality coefficients):

Parameter proportional to heat radiation $$x_1 = a_1 \times (T_3)^4$$

Parameter proportional to heat convection $$x_2 = a_2 \times (T_4 - T_3)$$

Parameter proportional to hemoglobin concentration $$x_3 = a_3 \times \left(\frac{A_1}{a \times A_{HbO_2}(810 \text{ nm})}\right)$$

Parameter proportional to hemoglobin oxygen saturation $$x_4 = a_4 \times \left(\frac{A_2 \times A_{HbO_2}(810 \text{ nm}) - A_1 \times A_{Hb}(950 \text{ nm}))}{A_1 \times (A_{HbO_2}(950 \text{ nm}) - A_{Hb}(950 \text{ nm}))}\right)$$

Parameter proportional to blood flow volume $$x_5 = a_5 \times \left(\frac{1}{t_{CONT} \times (S_1 - S_2)}\right)$$

Then, normalized parameters are calculated from mean values and standard deviations of $x_i$ obtained by actual data pertaining to large numbers of able-bodied people and diabetic patients. A normalized parameter $X_i$ (where i=1, 2, 3, 4, 5) is calculated from each parameter $x_i$ according to the following equation:

$$X_i = \frac{x_i - \overline{x}_i}{SD(x_i)}$$

where $x_i$: parameter $\overline{x}_i$: mean value of the parameter $SD(x_i)$: standard deviation of the parameter Using the above five normalized parameters, calculations are conducted for conversion into glucose concentration to be eventually displayed. A program necessary for the processing calculations is stored in a ROM in the microprocessor built inside the apparatus. The memory area required for the processing calculations is ensured in a RAM similarly built inside the apparatus. The results of calculation are displayed on the LCD.

The ROM stores, as a constituent element of the program necessary for the processing calculations, a function for determining glucose concentration C in particular. The function is defined as follows. C is expressed by the below-indicated equation (1), where $a_i$ (i=0, 1, 2, 3, 4, 5) is determined from a plurality of pieces of measurement data in advance according to the following procedure:

(1) A multiple regression equation that indicates the relationship between the normalized parameter and the glucose concentration C is created.

(2) A normalized equation (simultaneous equation) relating to the normalized parameter is obtained from an equation obtained by the least-squares method.

(3) Values of coefficient $a_i$(i=0, 1, 2, 3, 4, 5) are determined from the normalized equation and then substituted into the multiple regression equation.

Initially, the regression equation (1) indicating the relationship between the glucose concentration C and the normalized parameters $X_1$, $X_2$, $X_3$, $X_4$, and $X_5$ is formulated.

$$C = f(X_1, X_2, X_3, X_4, X_5) \quad (1)$$
$$= a_0 + a_1 X_1 + a_2 X_2 + a_3 X_3 + a_4 X_4 + a_5 X_5$$

Then, the least-squares method is employed to obtain a multiple regression equation that would minimize the error with respect to a measured value Ci of glucose concentration according to an enzyme electrode method. When the sum of squares of the residual is D, D is expressed by the following equation (2):

$$D = \sum_{i=1}^{n} d_i^2 \quad (2)$$

$$= \sum_{i=1}^{n} (C_i - f(X_{i1}, X_{i2}, X_{i3}, X_{i4}, X_{i5}))^2$$

$$= \sum_{i=1}^{n} \{C_i - (a_0 + a_1 X_{i1} + a_2 X_{i2} + a_3 X_{i3} + a_4 X_{i4} + a_5 X_{i5})\}^2$$

Because the sum of squares of the residual D becomes minimum when partial differentiation of equation (2) with respect to $a_0, a_2, \ldots, a_5$ gives zero. Thus, we have the following equations:

$$\frac{\partial D}{\partial a_0} = -2 \sum_{i=1}^{n} \{C_i - (a_0 + a_1 X_{i1} + a_2 X_{i2} + a_3 X_{i3} + a_4 X_{i4} + a_5 X_{i5})\} \quad (3)$$
$$= 0$$

$$\frac{\partial D}{\partial a_1} = -2 \sum_{i=1}^{n} X_{i1} \{C_i - (a_0 + a_1 X_{i1} + a_2 X_{i2} + a_3 X_{i3} + a_4 X_{i4} + a_5 X_{i5})\}$$
$$= 0$$

$$\frac{\partial D}{\partial a_2} = -2 \sum_{i=1}^{n} X_{i2} \{C_i - (a_0 + a_1 X_{i1} + a_2 X_{i2} + a_3 X_{i3} + a_4 X_{i4} + a_5 X_{i5})\}$$
$$= 0$$

$$\frac{\partial D}{\partial a_3} = -2 \sum_{i=1}^{n} X_{i3} \{C_i - (a_0 + a_1 X_{i1} + a_2 X_{i2} + a_3 X_{i3} + a_4 X_{i4} + a_5 X_{i5})\}$$
$$= 0$$

$$\frac{\partial D}{\partial a_4} = -2 \sum_{i=1}^{n} X_{i4} \{C_i - (a_0 + a_1 X_{i1} + a_2 X_{i2} + a_3 X_{i3} + a_4 X_{i4} + a_5 X_{i5})\}$$
$$= 0$$

$$\frac{\partial D}{\partial a_5} = -2 \sum_{i=1}^{n} X_{i5} \{C_i - (a_0 + a_1 X_{i1} + a_2 X_{i2} + a_3 X_{i3} + a_4 X_{i4} + a_5 X_{i5})\}$$
$$= 0$$

When the mean values of C and $X_1$ to $X_5$ are $C_{mean}$ and $X_{1mean}$ to $X_{5mean}$, respectively, since $X_{imean}=0$ (i=1 to 5), equation (4) can be obtained from equation (1) thus:

$$a_0 = C_{mean} - a_1 X_{1mean} - a_2 X_{2mean} - a_3 X_{3mean} - a_4 X_{4mean} - a_5 X_{5mean} \quad (4)$$
$$= C_{mean}$$

The variation and covariation between the normalized parameters are expressed by equation (5). Covariation between the normalized parameter $X_i$ (i=1 to 5) and C is expressed by equation (6).

$$S_{ij} = \sum_{k=1}^{n} (X_{ki} - X_{imean})(X_{kj} - X_{jmean}) = \sum_{k=1}^{n} X_{ki} X_{kj} \quad (i, j = 1, 2, \ldots 5) \quad (5)$$

$$S_{iC} = \sum_{k=1}^{n} (X_{ki} - X_{imean})(C_k - C_{mean}) \quad (6)$$

$$= \sum_{k=1}^{n} X_{ki}(C_k - C_{mean}) \quad (i = 1, 2, \ldots 5)$$

Substituting equations (4), (5), and (6) into equation (3) and rearranging yields simultaneous equation (normalized equation) (7). Solving equation (7) yields $a_1$ to $a_5$.

$$a_1 S_{11} + a_2 S_{12} + a_3 S_{13} + a_4 S_{14} + a_5 S_{15} = S_{1C}$$

$$a_1 S_{21} + a_2 S_{22} + a_3 S_{23} + a_4 S_{24} + a_5 S_{25} = S_{2C}$$

$$a_1 S_{31} + a_2 S_{32} + a_3 S_{33} + a_4 S_{34} + a_5 S_{35} = S_{3C}$$

$$a_1 S_{41} + a_2 S_{42} + a_3 S_{43} + a_4 S_{44} + a_5 S_{45} = S_{4C}$$

$$a_1 S_{51} + a_2 S_{52} + a_3 S_{53} + a_4 S_{54} + a_5 S_{55} = S_{5C} \quad (7)$$

Constant term $a_0$ is obtained by means of equation (4). The thus obtained $a_i$ (i=0, 1, 2, 3, 4, 5) is stored in ROM at the time of manufacture of the apparatus. In actual measurement using the apparatus, the normalized parameters $X_1$ to $X_5$ obtained from the measured values are substituted into regression equation (1) to calculate the glucose concentration C.

Hereafter, an example of the process of calculating the glucose concentration will be described. The coefficients in equation (1) are determined in advance based on large data obtained from able-bodied persons and diabetic patients. The ROM in the microprocessor stores the following formula for the calculation of glucose concentration:

$$C = 99.4 + 18.3 \times X_1 - 20.2 \times X_2 - 23.7 \times X_3 - 22.0 \times X_4 - 25.9 \times X_5$$

$X_1$ to $X_5$ are the results of normalization of parameters $x_1$ to $x_5$. Assuming the distribution of the parameters is normal, 95% of the normalized parameter takes on values between −2 to +2.

In the case of an able-bodied person, substituting exemplary measurement values in the above equation such that $X_1=-0.06$, $X_2=+0.04$, $X_3=+0.05$, $X_4=-0.12$, and $X_5=+0.10$ yields C=96 mg/dl. In the case of a diabetic patient, substituting exemplary measurement values in the equation such that $X_1=+1.15$, $X_2=-1.02$, $X_3=-0.83$, $X_4=-0.91$, and $X_5=-1.24$ yields C=213 mg/dl.

Hereafter, the results of measurement by the conventional enzymatic electrode method and those by the method of the invention will be compared. In the enzymatic electrode method, a blood sample is reacted with a reagent and the amount of resultant electrons is measured to determine glucose concentration. When the glucose concentration for an able-bodied person was 89 mg/dl according to the enzymatic electrode method, the normalized parameters obtained by measurement at the same time according to the invention were $X_1=-0.06$, $X_2=+0.04$, $X_3=+0.05$, $X_4=-0.12$, and $X_5=+0.10$. Substituting these values into the above equation yields C=96 mg/dl. On the other hand, when the glucose concentration for a diabetic patient was 238 mg/dl according to the enzymatic electrode method, the normalized parameters obtained by measurement at the same time according to the invention were $X_1=+1.15$, $X_2=-1.02$, $X_3=-0.83$, $X_4=-0.91$, and $X_5=-1.24$. Substituting these values into the above equation yields C=213 mg/dl. The results thus indicated that the method according to the invention can provide highly accurate glucose concentration.

Figure 9:
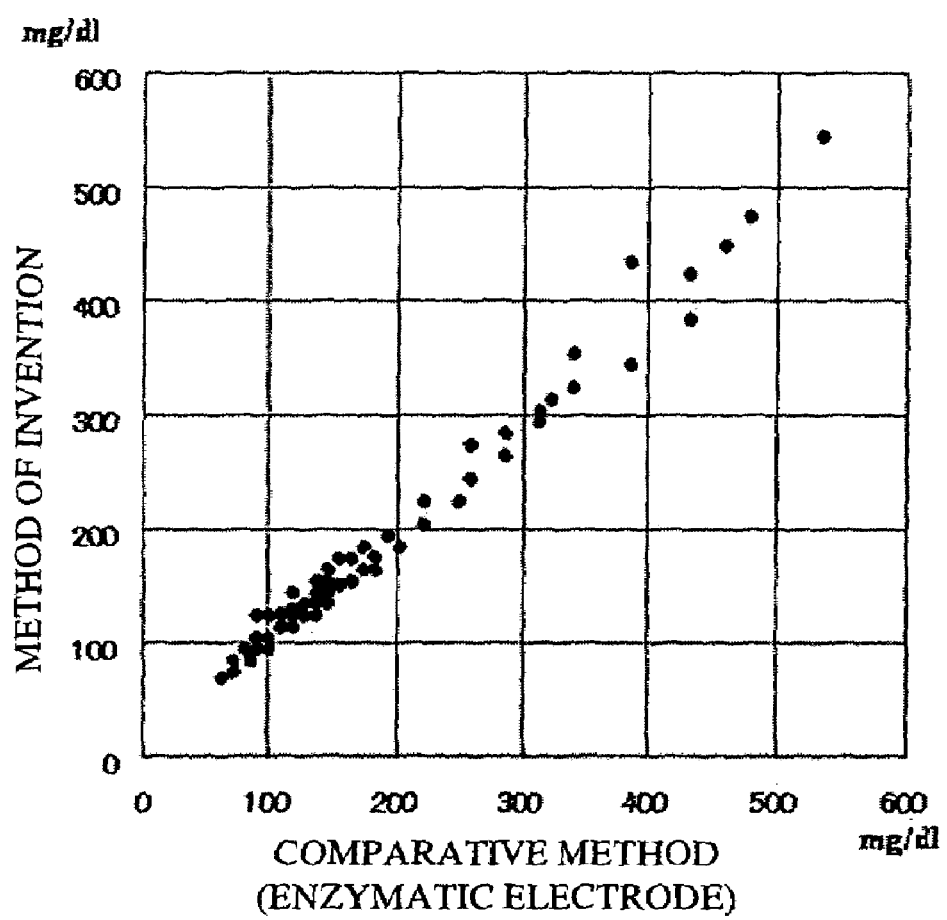
FIG. 9 shows the plots of the glucose concentration values calculated according to the present invention and the glucose concentration values measured by the enzymatic electrode method.

FIG. 9 shows the plot of glucose concentration for a plurality of patients. The calculated values of glucose concentration according to the invention are shown on the vertical axis, and the measured values of glucose concentration according to the enzymatic electrode method are shown on the horizontal axis. It will be seen that a good correlation can be obtained by measuring the oxygen supply volume and the blood flow volume according to the method of the invention (correlation coefficient=0.9324).

Thus, the invention can provide a highly accurate non-invasive blood sugar level measuring apparatus and method.

What is claimed is:

1. A blood sugar level measuring apparatus comprising:
   a heat amount measuring unit for measuring a plurality of temperatures derived from the body surface in order to obtain information used for calculating the amount of convective heat transfer and the amount of radiation heat transfer concerning the dissipation of heat from the body surface;
   an oxygen volume measuring unit for obtaining information concerning the volume of blood oxygen;
   a storage unit for storing the relationships between blood sugar levels and the individual parameters corresponding to both the multiple temperatures and blood oxygen volume;
   a computing unit for converting the measurement values provided by the heat amount measuring unit and the oxygen volume measuring unit into parameters, and computing a blood sugar level by applying the parameters to the relationships stored in the storage unit; and
   a display unit for displaying the blood sugar level computed by the computing unit.

2. The blood sugar level measuring apparatus according to claim 1, wherein the oxygen volume measuring unit comprises a blood flow volume measuring unit for obtaining information concerning the volume of blood flow, and an optical measuring unit for obtaining blood hemoglobin concentration and hemoglobin oxygen saturation.

3. The blood sugar level measuring apparatus according to claim 2, wherein the blood flow volume measuring unit further comprises:
   a body-surface contact unit; and
   an adjacent temperature detector disposed adjacent the body-surface contact unit.

4. A blood sugar level measuring apparatus comprising:
   a heat amount measuring unit for measuring a plurality of temperatures derived from the body surface in order to obtain information used for calculating the amount of convective heat transfer and the amount of radiation heat transfer concerning the dissipation of heat from the body surface;
   an oxygen volume measuring unit for obtaining information concerning the volume of blood oxygen, wherein the oxygen volume measuring unit comprises a blood flow volume measuring unit for obtaining information concerning the volume of blood flow, and an optical measuring unit for obtaining blood hemoglobin concentration and hemoglobin oxygen saturation, wherein the blood flow volume measuring unit comprises a body-surface contact unit; an indirect temperature detector for detecting the temperature at a position distanced away from the body-surface contact unit; and
   a heat conducting member connecting the body-surface contact unit and the indirect temperature detector;
   a storage unit for storing the relationships between blood sugar levels and the individual parameters corresponding to both the multiple temperatures and blood oxygen volume;
   a computing unit for converting the measurement values provided by the heat amount measuring unit and the oxygen volume measuring unit into parameters, and computing a blood sugar level by applying the parameters to the relationships stored in the storage unit; and
   a display unit for displaying the blood sugar level computed by the computing unit.

5. The blood sugar level measuring apparatus according to claim 4, wherein the optical measuring unit comprises:
   a light source for generating light of at least two different wavelengths;
   an optical system for irradiating the body surface with light emitted by the light source; and
   a photodetector for detecting the light reflected by the body surface.

6. The blood sugar level measuring apparatus according to claim 5, wherein the results of detection by the photodetector are used for computing blood hemoglobin concentration and hemoglobin oxygen saturation.

7. The blood sugar level measuring apparatus according to claim 4, wherein the heat amount measuring unit comprises:
   an ambient temperature detector for measuring the ambient temperature; and
   a radiation temperature detector for measuring the radiation heat from the body surface.

8. A non-invasive blood sugar level measuring apparatus comprising:
   a temperature measuring unit for measuring a plurality of temperatures from a body surface;
   a blood flow volume measuring unit for obtaining information concerning the volume of blood flow based on the results of measurement by the temperature measuring unit;
   an oxygen volume measuring unit for determining the volume of blood oxygen based on the result of measurement by the blood flow volume measuring unit;
   a storage unit for storing the relationships between blood sugar levels and individual parameters corresponding to the multiple temperatures, the volume of blood oxygen and the volume of blood flow;
   a computing unit for converting the measurement values provided by the temperature measuring unit, the blood flow volume measuring unit and the oxygen volume measuring unit into parameters, and computing a blood sugar level by applying the parameters to the relationships stored in the storage unit; and
   a display unit for displaying the blood sugar level computed by the computing unit.

9. The blood sugar level measuring unit according to claim 8, wherein the blood flow volume measuring unit comprises:
   a body-surface contact unit;
   an adjacent temperature detector disposed adjacent the body-surface contact unit;
   an indirect temperature detector for detecting the temperature at a position distanced away from the body-surface contact unit; and
   a heat conducting member connecting the body-surface contact unit and the indirect temperature detector.

10. The blood sugar level measuring apparatus according to claim 8, further comprising an optical measuring unit, the oxygen volume measuring unit comprising:
a light source for generating light of at least two different wavelengths;
an optical system for irradiating the body surface with light emitted by the light source; and
a photodetector for detecting the light reflected by the body surface, wherein
the oxygen volume measuring unit further employs the result of detection by the photodetector in determining the volume of blood oxygen.

11. The blood sugar level measuring apparatus according to claim 10, wherein the result of detection by the photodetector is used in calculating the blood hemoglobin concentration and hemoglobin oxygen saturation.

12. A blood sugar level measuring apparatus comprising:
an ambient temperature measuring unit for measuring the ambient temperature;
a body-surface contact unit to be brought into contact with a body surface;
a radiation heat detector for measuring the radiation heat from the body surface;
a heat conducting member disposed in contact with the body-surface contact unit;
an indirect temperature detector disposed adjacent the heat conducting member and away from the body-surface contact unit for detecting the temperature at a position distanced away from the body-surface contact unit;
a light source for irradiating the body-surface contact unit with light of at least two different wavelengths;
a photodetector for detecting reflected light produced as the light from the light source is reflected by the body surface;
a computing unit comprising a converting portion and a processing portion, wherein the converting portion converts the outputs of the indirect temperature detector, the ambient temperature measuring unit, the radiation heat detector, and the photodetector into individual parameters, and wherein the processing portion stores the relationships between the parameters and blood sugar levels in advance and computes a blood sugar level by applying the parameters to the stored relationships; and
a display unit for displaying the blood sugar level produced by the computing unit.

13. The blood sugar level measuring apparatus according to claim 12, wherein the light is used for measuring the blood hemoglobin concentration and hemoglobin oxygen saturation.

14. The blood sugar level measuring apparatus according to claim 12, further comprising:
a plate adapted to cover an opening end of the heat conducting member in contact with the body-surface contact unit; and
an adjacent temperature detector for detecting the temperature of the plate, wherein
the output of the adjacent temperature detector is converted into a parameter by the converter unit.

15. The blood sugar level measuring apparatus according to claim 14, wherein the thermal conductivity of the plate is higher than that of the heat conducting member.

16. The blood sugar level measuring apparatus according to claim 12, further comprising:
a first optical fiber connecting the light source and the body-surface contact unit; and
a second optical fiber connecting the body-surface contact unit and the photodetector, wherein
the body surface is irradiated with the light from the light source transmitted via the first optical fiber, and the reflected light is guided to the photodetector via the second optical fiber.

17. The blood sugar level measuring apparatus according to claim 12, further comprising an infrared lens disposed between the body-surface contact unit and the indirect temperature detector.

18. A blood sugar level measuring apparatus comprising:
an ambient temperature measuring unit for measuring the ambient temperature;
a body-surface contact unit to be brought into contact with a body surface;
a heat conducting member disposed in contact with a first region of the body-surface contact unit;
an indirect temperature detector disposed adjacent the heat conductive member and away from the body-surface contact unit for detecting the temperature at a position distanced away from the body-surface contact unit;
a cylindrical member disposed in contact with a second region of the body-surface contact unit and having an opening on one end thereof;
a radiation heat detector disposed adjacent the other end of the cylindrical member for measuring the radiation heat from the body surface;
a light source for irradiating the one end of the cylindrical member with light of at least two different wavelengths;
a photodetector for detecting reflected light produced by the reflection of the light by the body surface;
a computing unit comprising a converting portion and a processing portion, wherein the converting portion converts the outputs of the indirect temperature detector, the ambient temperature measuring unit, the radiation temperature detector, and the photodetector into individual parameters, and wherein the processing portion stores the relationships between the parameters and blood sugar levels in advance and computes a blood sugar level by applying the parameters to the relationships; and
a display unit for displaying the blood sugar level produced by the computing unit.

19. The blood sugar level measuring apparatus according to claim 18, wherein the first and the second regions are disposed adjacent to each other.

20. The blood sugar level measuring apparatus according to claim 18, further comprising:
a first optical fiber connecting the light source and the one end of the cylindrical member; and
a second optical fiber connecting the one end and the photodetector, wherein
the light emitted by the light source is guided through the first optical fiber and is then shone on the body surface, and the reflected light is guided through the second optical fiber onto the photodetector.

21. The blood sugar level measuring apparatus according to claim 18, further comprising an infrared lens disposed between the second region and the indirect temperature detector.

* * * * *